(12) United States Patent
Ozawa et al.

(10) Patent No.: US 11,484,214 B2
(45) Date of Patent: Nov. 1, 2022

(54) BIOLOGICAL INFORMATION MEASURING DEVICE

(71) Applicants: OMRON Corporation, Kyoto (JP); OMRON HEALTHCARE CO., LTD., Kyoto (JP)

(72) Inventors: Hisashi Ozawa, Kyoto (JP); Keigo Kamada, Tokyo (JP); Satoshi Yase, Nara (JP); Ayaka Iwade, Nara (JP); Masayuki Sugano, Uji (JP); Keisuke Saito, Suita (JP); Yasuhiro Kawabata, Kyoto (JP)

(73) Assignees: OMRON Corporation, Kyoto (JP); OMRON HEALTHCARE CO., LTD., Kyoto (JP)

( * ) Notice: Subject to any disclaimer, the term of this patent is extended or adjusted under 35 U.S.C. 154(b) by 217 days.

(21) Appl. No.: 16/970,946

(22) PCT Filed: Feb. 26, 2019

(86) PCT No.: PCT/JP2019/007327
§ 371 (c)(1),
(2) Date: Aug. 18, 2020

(87) PCT Pub. No.: WO2019/176529
PCT Pub. Date: Sep. 19, 2019

(65) Prior Publication Data
US 2020/0390338 A1    Dec. 17, 2020

(30) Foreign Application Priority Data
Mar. 14, 2018  (JP) .............................. JP2018-046991

(51) Int. Cl.
*A61B 5/022*  (2006.01)
*A61B 5/00*   (2006.01)
(Continued)

(52) U.S. Cl.
CPC ............ *A61B 5/022* (2013.01); *A61B 5/0015* (2013.01); *A61B 5/02141* (2013.01);
(Continued)

(58) Field of Classification Search
CPC ... A61B 5/022; A61B 5/0015; A61B 5/02141; A61B 5/6824; A61B 5/6831; A61B 5/0507
See application file for complete search history.

(56) References Cited

U.S. PATENT DOCUMENTS

2004/0147848 A1* 7/2004 Shirasaki ........... A61B 5/02116
600/490
2006/0094937 A1   5/2006 Immoreev et al.
(Continued)

FOREIGN PATENT DOCUMENTS

JP   2005102959   4/2005
JP   2013132437   7/2013
(Continued)

OTHER PUBLICATIONS

"International Search Report (Form PCT/ISA/210) of PCT/JP2019/007327," dated May 28, 2019, with English translation thereof, pp. 1-4.
(Continued)

*Primary Examiner* — Allen Porter
*Assistant Examiner* — Abid A Mustansir
(74) *Attorney, Agent, or Firm* — JCIPRNET

(57) ABSTRACT

An embodiment of the present invention provides a sphygmomanometer that is worn on a measured part of the left wrist of a subject (user) for use. In the sphygmomanometer, on an inner peripheral surface of a band-like body that constitutes a base of a band, a portion for installing a pressure cuff and a protrusion for installing an antenna substrate are separately provided, and the pressure cuff and
(Continued)

the antenna substrate are respectively installed on these portions.

10 Claims, 10 Drawing Sheets

(51) Int. Cl.
*A61B 5/021* (2006.01)
*A61B 5/0507* (2021.01)

(52) U.S. Cl.
CPC .......... *A61B 5/0507* (2013.01); *A61B 5/6824* (2013.01); *A61B 5/6831* (2013.01)

(56) References Cited

U.S. PATENT DOCUMENTS

2017/0215748 A1* 8/2017 Jang ................. A61B 5/6824
2019/0053741 A1* 2/2019 Chaudhry ............ A61B 5/7246

FOREIGN PATENT DOCUMENTS

| JP | 2013543777 | 12/2013 |
| JP | 2015077395 | 4/2015 |
| JP | 2017500845 | 1/2017 |
| JP | 2017176340 | 10/2017 |
| WO | 2016009315 | 1/2016 |

OTHER PUBLICATIONS

"Written Opinion of the International Searching Authourity (Form/ISA/237) of PCT/JP2019/007327", dated May 28, 2019, with English translation thereof, p. 1-p. 6.

* cited by examiner

BIOLOGICAL INFORMATION MEASURING DEVICE

CROSS-REFERENCE TO RELATED APPLICATION

This application is a 371 application of the International PCT application serial no. PCT/JP2019/007327, filed on Feb. 26, 2019, which claims the priority benefit of Japan Patent Application No. 2018-046991, filed on Mar. 14, 2018. The entirety of each of the above-mentioned patent applications is hereby incorporated by reference herein and made a part of this specification.

TECHNICAL FIELD

An embodiment of the present invention relates to a biological information measuring device including, for example, a functional unit that measures blood pressure using a pressure cuff and a functional unit that measures a pulse wave of an artery using radio waves.

RELATED ART

Conventionally, as one of biological information measuring devices, there has been known a device including, for example, a functional unit that measures blood pressure of a subject by compressing a measured part such as an upper arm or a wrist or the like of the subject with a pressure cuff and measuring a pressure thereof, and a functional unit that measures a pulse wave of the subject by disposing a pair of a transmitting antenna and a receiving antenna to face the measured part including an artery of the subject, transmitting a radio wave (measurement signal) from the transmitting antenna to the measured part and receiving a reflected wave (reflection signal) of the measurement signal from the measured part by the receiving antenna (for example, see Patent Document 1).

PRIOR-ART DOCUMENTS

Patent Documents

Patent Document 1: Japanese Patent Laid-open No. 2013-132437

SUMMARY OF THE INVENTION

Problems to be Solved by the Invention

However, a conventional biological information measuring device having both a blood pressure measurement function by an oscillometric method and a pulse wave measurement function using radio waves has, for example, a structure in which a transmitting antenna and a receiving antenna for pulse wave measurement are attached to a pressing surface of the pressure cuff, that is, the surface in contact with the skin. Hence, there has been a fear that the attachment state of the transmitting antenna and the receiving antenna with respect to the pressure cuff may deteriorate and the transmitting antenna and the receiving antenna may fall off or be deformed or the like during repeated pressurization and depressurization of the pressure cuff, and there has been a concern that reliability of the device may be reduced. In addition, since the transmitting antenna and the receiving antenna are pressed against the skin of the subject by the pressurization of the pressure cuff, the subject may feel discomfort such as pain on the skin or the like.

The present invention has been made in view of the above circumstances, and attempts to provide a biological information measuring device that improves the reliability of the device and reduces the discomfort to the subject.

Means for Solving the Problems

In order to solve the above problems, a first aspect of a biological information measuring device according to the present invention includes: a band-shaped band member, worn so as to surround a measured part including an artery of a living body; a pressing member, disposed on a surface of the band member that faces the measured part, expanding due to injection of a fluid during blood pressure measurement and pressing the measured part; and an antenna support member, installed on a portion of the surface of the band member that faces the measured part, where the pressing member is not disposed. An antenna element is installed on the antenna support member in a state in which the band member is worn on and is in contact with the measured part. The antenna element operates so as to transmit a measurement signal composed of a radio wave to the measured part and to receive a reflection signal of the measurement signal from the measured part.

According to the first aspect of the present invention, the antenna support member is not attached to a pressing surface of the pressing member but is installed at a position in the band member where the pressing member is not disposed. Hence, even if pressurization and depressurization of the pressing member are repeated, the installation state of the antenna support member does not deteriorate. Accordingly, the occurrence of problems such as falling or deformation or the like of the antenna support member is prevented, and the reliability of the device can be enhanced. In addition, since the antenna support member has a structure that cannot be pressed against the skin of the subject by the pressurization of the pressure cuff, there is no concern that the subject will feel discomfort such as pain or the like.

A second aspect of the biological information measuring device according to the present invention is as follows. In the first aspect, a plurality of the antenna support members are disposed at predetermined intervals in a direction along the artery included in the measured part.

A third aspect of the biological information measuring device according to the present invention is as follows. In the first aspect, a plurality of the antenna elements are disposed on one antenna support member at predetermined intervals in a direction along the artery included in the measured part.

According to the second and third aspects of the present invention, the transmission of the measurement signal and the reception of the reflection signal are performed at a plurality of different positions on an upstream side and a downstream side of one artery. Hence, it becomes possible to detect pulse wave signals at different positions in the artery, and it becomes possible to perform blood pressure estimation focused on pulse transit time (PTT) based on these pulse wave signals.

A fourth aspect of the biological information measuring device according to the present invention is as follows. In the first or second aspect, a plurality of the antenna support members are disposed at predetermined intervals in a direction orthogonal to the artery included in the measured part.

A fifth aspect of the biological information measuring device according to the present invention is as follows. In the first or third aspect, a plurality of the antenna elements are disposed on one antenna support member at predetermined intervals in a direction orthogonal to the artery included in the measured part.

According to the fourth and fifth aspects of the present invention, the transmission and reception of the measurement signal and the reflection signal are respectively performed at a plurality of positions in the direction orthogonal to the artery. Hence, for example, although the position of the artery of the subject differs from person to person, and even if the wearing position of the device with respect to the measured part shifts in the direction orthogonal to the artery, it becomes possible to bring at least one of the plurality of antenna support members close to the artery. Accordingly, it becomes possible to measure a pulse wave representing the motion of the artery with good quality.

A sixth aspect of the biological information measuring device according to the present invention is configured as follows. In any one of the first to fifth aspects, on the surface of the band member that faces the measured part, a protrusion whose height is set based on a thickness dimension of the pressing member at the time of contraction is provided, and the antenna support member is disposed on the protrusion.

According to the sixth aspect of the present invention, it becomes possible for the antenna support member to abut against the measured part of the subject with an appropriate pressure.

A seventh aspect of the biological information measuring device according to the present invention is configured as follows. In any one of the first to fifth aspects, on the surface of the band member that faces the measured part, a band-shaped recess having a shape corresponding to the pressing member and a protrusion having a predetermined height for the antenna support member to abut against the measured part are provided. The pressing member is disposed in the recess, and the antenna support member is disposed on the protrusion.

According to the seventh aspect of the present invention, since the pressing member is disposed in the band-shaped recess provided in the band member, it becomes possible to stably maintain the disposition position of the pressing member with respect to the band member. Accordingly, for example, a problem such as that the pressing member may contact or overlap the antenna support member can be prevented.

An eighth aspect of the biological information measuring device according to the present invention is configured as follows. In any one of the first to seventh aspects, a control circuit support member electrically connected to the antenna support member is disposed between the band member and the pressing member. In this control circuit support member, at least a transmitting circuit generating the measurement signal and supplying power to the antenna element, and a receiving circuit receiving the reflection signal received by the antenna element and detecting a pulse wave signal representing the motion of the measured part from the reflection signal are provided.

According to the eighth aspect of the present invention, it becomes possible to dispose the control circuit support member at a position close to the antenna support member. Hence, it becomes possible to transmit the measurement signal and the reflection signal between the control circuit support member and the antenna support member without large attenuation. Accordingly, a signal-to-noise ratio of the pulse wave signal can be increased.

Effects of the Invention

That is, according to each aspect of the present invention, a biological information measuring device that improves the reliability of the device and reduces the discomfort to the subject can be provided.

DESCRIPTION OF THE EMBODIMENTS

An embodiment of the present invention is hereinafter described with reference to the drawings.

[Application Example]

First, one of application examples of a biological information measuring device according to one embodiment of the present invention is described.

The biological information measuring device according to one embodiment of the present invention includes a first blood pressure measuring part estimating blood pressure based on pulse transit time (PTT) and a second blood pressure measuring part measuring the blood pressure by an oscillometric method.

For example, at two different positions in a measured part such as a wrist or an upper arm or the like where an artery is present, the first blood pressure measuring part that uses PTT measures a pulse wave representing the motion of the above artery by transmitting a radio wave to the above artery and receiving a reflected wave thereof, and calculates the PTT based on the measurement result. Then, a blood pressure value is estimated by using a calculated value of the PTT and a predetermined relationship between PTT and blood pressure value.

The second blood pressure measuring part that uses the oscillometric method measures the blood pressure by measuring the pressure of the pulse wave in a process of pressurizing and then depressurizing a pressure cuff in a state in which the pressure cuff is wound around the measured part such as the wrist or the upper arm or the like where the artery is present.

To realize the blood pressure measurement based on PTT and the blood pressure measurement by the oscillometric method mentioned above with one device, it is necessary to install both the pressure cuff, and an antenna substrate as an antenna support member having an antenna element transmitting and receiving the radio wave to and from the measured part. As an installation structure of the antenna substrate and the pressure cuff, a general structure is that the antenna substrate is installed on a pressing surface (that is, a surface in contact with the measured part) of the pressure cuff. However, in such a structure, there is a fear that the installation state of the antenna substrate with respect to the pressure cuff may deteriorate and the antenna substrate may fall off or be deformed or the like during repeated pressurization and depressurization of the pressure cuff, and there is a concern that the reliability of the device may be reduced. In addition, each time the pressure cuff is pressurized, the antenna substrate is pressed against the skin of a subject by the pressure of the pressure cuff. Therefore, there is a concern that the subject may feel discomfort such as pain or the like on the skin.

Figure 5:
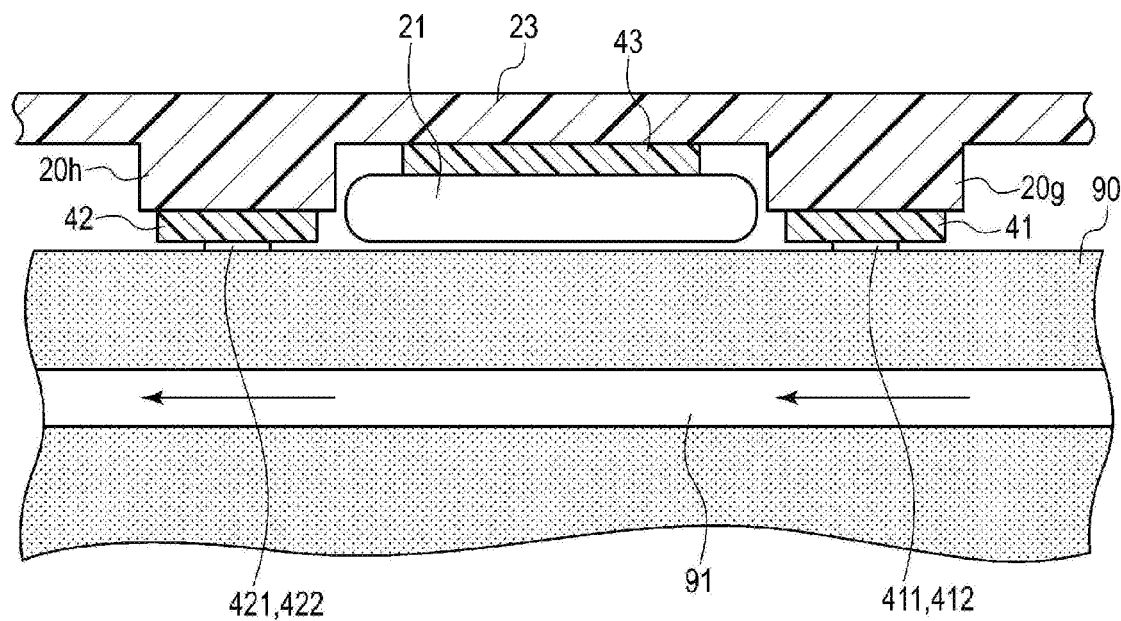
FIG. 5 is a sectional view showing a contact state of an antenna substrate and a pressure cuff with respect to the wrist when the biological information measuring device shown in FIG. 1 is worn on the left wrist.

Therefore, in one embodiment of the present invention, for example, as shown in FIG. 5, on a band (for example, a band-like body composed of a resin member) 23 for wearing the device on the measured part such as the left wrist or the like of the subject (user), a portion for installing a pressure cuff 21 and protrusions 20g and 20h for installing antenna substrates 41 and 42 are provided, and the pressure cuff 21 and the antenna substrates 41 and 42 are configured to be respectively installed on these portions. Moreover, 412 and 422 denote antenna elements provided on the antenna substrates 41 and 42, and 43 denotes a control circuit board as a control circuit support member connected to the antenna substrates 41 and 42.

With such a configuration, the following effects can be achieved. That is, the antenna substrates 41 and 42 are installed on the protrusions 20g and 20h formed on the band-like body 23 of a band 20, instead of on a pressing surface of the pressure cuff 21. Hence, even if the pressurization and depressurization of the pressure cuff 21 are repeated, there is no concern that a deterioration of the installation state, such as deformation or falling or the like, may occur in the antenna substrates 41 and 42. Accordingly, the reliability of the device can be maintained high.

In addition, in a state in which the device is worn on a measured part 90 of the subject, the antenna substrates 41 and 42 contact the skin of the measured part 90 independently of the pressure cuff 21. Hence, when the pressure cuff 21 is pressurized, the antenna substrates 41 and 42 will not be strongly pressed against the skin surface by the pressure of the pressure cuff 21. Thus, there is no longer a concern that the subject may feel discomfort such as pain or the like on the skin. Accordingly, stress on the subject during use can be reduced.

Further, since the protrusions 20g and 20h are formed on the band-like body 23 of the band 20 and the antenna substrates 41 and 42 are installed on the protrusions 20g and 20h, the antenna substrates 41 and 42 are able to stably contact the skin surface of the subject with an always constant pressure. Hence, it is possible to reduce the reflection and attenuation of the radio wave due to the skin surface of the measured part and to improve signal quality of the pulse wave.

One Embodiment (Configuration Example)
(1) Device Structure

Figure 1:
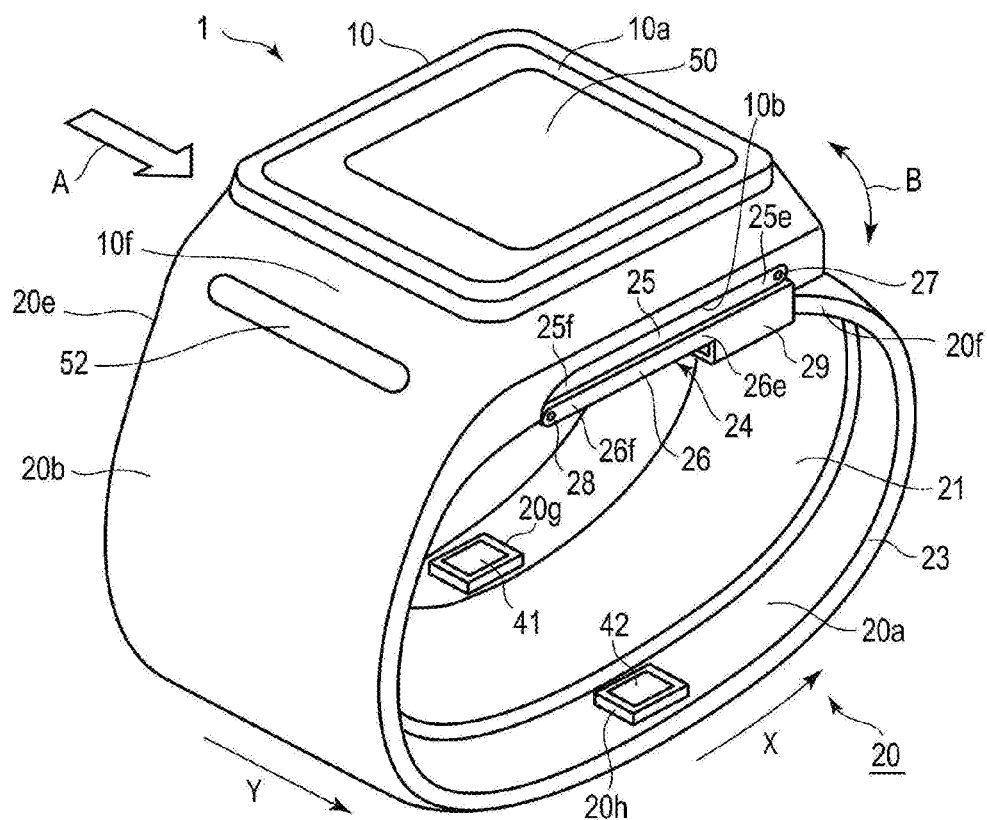
FIG. 1 is a perspective view showing an appearance of a biological information measuring device according to one embodiment of the present invention.
Figure 2:
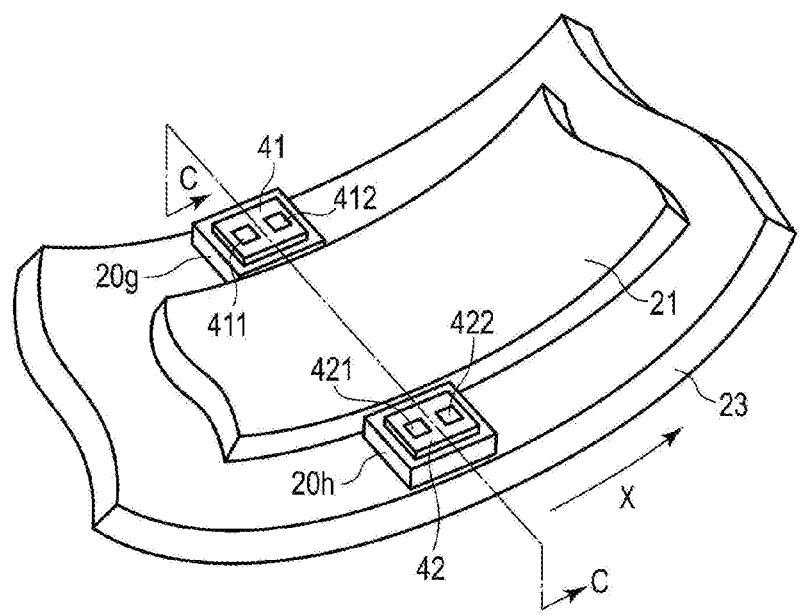
FIG. 2 is an enlarged perspective view showing a main part of the biological information measuring device shown in FIG. 1.
Figure 3:
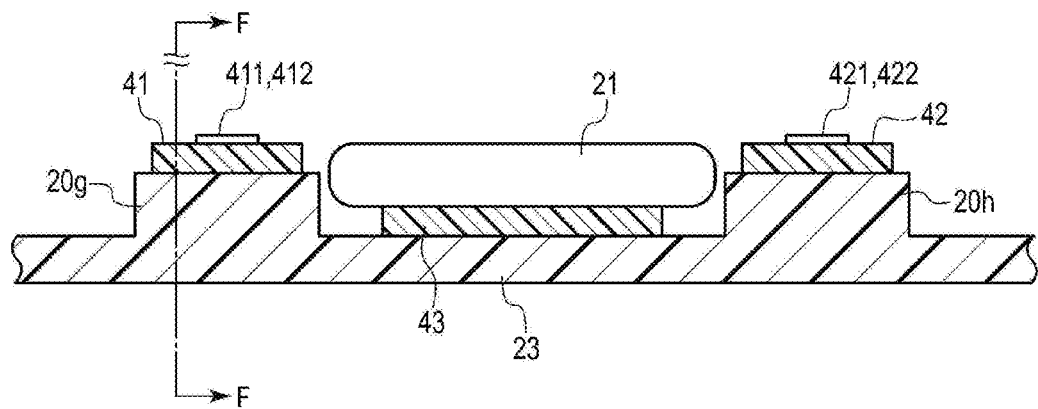
FIG. 3 is a diagram showing a section of the main part shown in FIG. 2 taken along arrow C-C.

FIG. 1 is a perspective view showing an overall structure of a biological information measuring device according to one embodiment of the present invention. FIG. 2 is an enlarged view showing a main part of the biological information measuring device shown in FIG. 1. FIG. 3 is a sectional view taken along arrow C-C of FIG. 2.

The biological information measuring device according to one embodiment is a wrist-type sphygmomanometer 1 that is worn on the left wrist of the subject for use. The sphygmomanometer 1 includes the band 20 worn on the left wrist of the user so as to surround an outer periphery thereof, and a main body 10 integrally attached to the band 20.

The band 20 has an elongated band-like shape so as to surround the left wrist along an outer peripheral direction thereof, and has an inner peripheral surface 20a in contact with the left wrist and an outer peripheral surface 20b opposite the inner peripheral surface 20a. A dimension (width dimension) of the band 20 in a width direction Y is set to about 35 mm to 40 mm in this example, but it may be set to other values.

The main body 10 is integrally provided (by integral molding in this example) on one end 20e of the band 20 in the outer peripheral direction. Moreover, the band 20 and the main body 10 may also be separately formed, and the main body 10 may be integrally attached to the band 20 via an engagement member (for example, a hinge or the like). In this example, it is assumed that a portion where the main body 10 is disposed corresponds to a dorsal surface (surface on the back side of the hand) of the left wrist in a wearing state.

The main body 10 has a three-dimensional shape having a thickness in a direction perpendicular to the outer peripheral surface 20b of the band 20. The main body 10 is formed to be small and thin so as not to disturb the user's daily activities. In this example, the main body 10 has a contour in a truncated square pyramid shape protruding outward from the band 20.

An indicator 50 displaying a screen is provided on a top surface (surface farthest from the measured part) 10a of the main body 10. In addition, an operation part 52 for inputting an instruction from the user is provided along a side surface (side surface on a left front side in FIG. 1) 10f of the main body 10.

A bottom surface (surface closest to the measured part) 10b of the main body 10 and an end 20f of the band 20 are connected by a trifold buckle 24. The buckle 24 includes a first plate member 25 disposed on an outer peripheral side and a second plate member 26 disposed on an inner peripheral side. One end 25e of the first plate member 25 is rotatably attached to the main body 10 via a connecting rod 27 extending along the width direction Y. The other end 25f of the first plate member 25 is rotatably attached to one end 26e of the second plate member 26 via a connecting rod 28 extending along the width direction Y. The other end 26f of the second plate member 26 is fixed to the vicinity of the end 20f of the band 20 by a fixing part 29.

Moreover, an attachment position of the fixing part 29 in a circumferential direction (X direction) of the band 20 is variably set in advance in accordance with a length of an outer circumference of the user's left wrist. Accordingly, the sphygmomanometer 1 (band 20) is configured in a substantially annular shape as a whole, and the bottom surface 10b of the main body 10 and the end 20f of the band 20 can be opened and closed by the buckle 24 in a direction of arrow B.

When wearing the sphygmomanometer 1 on the left wrist, with the buckle 24 open and a diameter of the ring of the band 20 increased, the user who is the subject puts their left hand through the band 20 in a direction indicated by arrow A in FIG. 1. Then, the user adjusts the position of the band 20 in a circumferential direction of the left wrist, and sets the antenna substrates (to be described later in detail) 41 and 42 installed on the inner peripheral surface of the band 20 to face each other on the radial artery passing through the left wrist. Accordingly, transmitting and receiving antenna pairs respectively provided on the antenna substrates 41 and 42 abut against a portion of a volar surface of the left wrist that corresponds to the radial artery. In this state, the user closes and fixes the buckle 24. In this way, the user wears the sphygmomanometer 1 on the left wrist.

Figure 4:
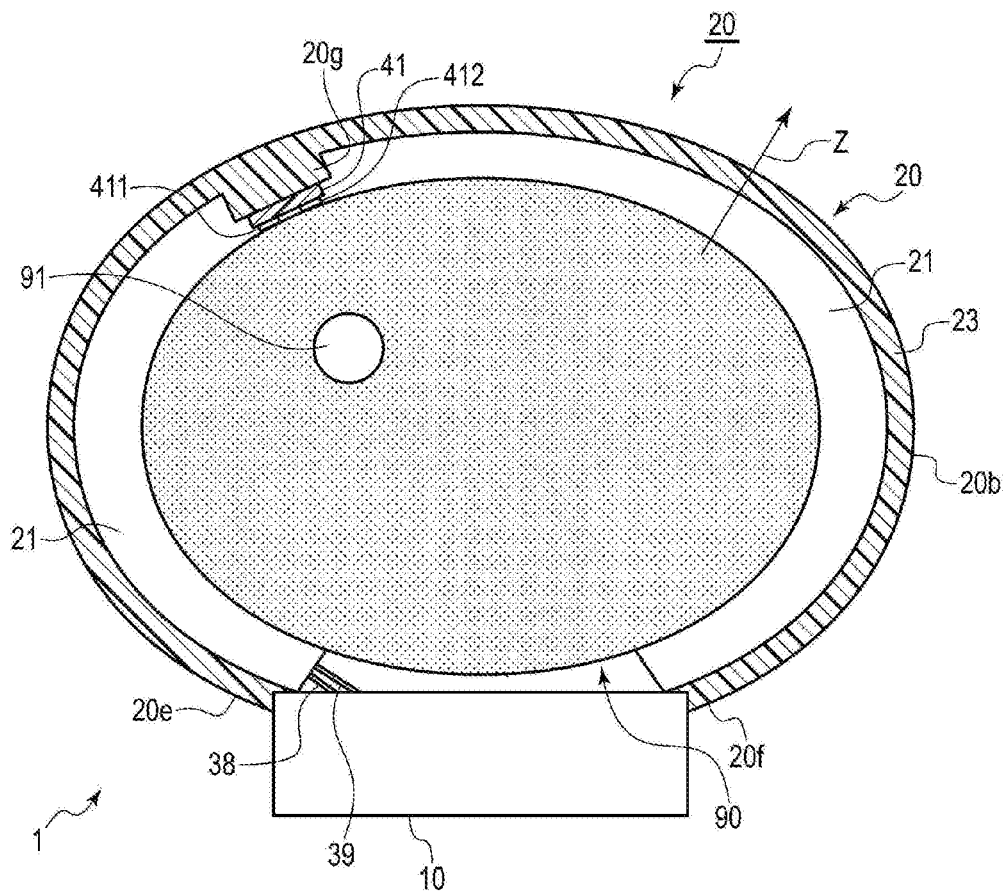
FIG. 4 is a sectional view taken along arrow F-F of FIG. 3, showing one example of a state in which the biological information measuring device shown in FIG. 1 is worn on the left wrist.

FIG. 4 shows one example of a state in which the sphygmomanometer 1 is worn on the left wrist 90 of the user and is a sectional view taken along arrow F-F of FIG. 3. FIG. 5 is an enlarged longitudinal sectional view showing a main part of FIG. 4.

The band 20 has the band-like body 23 that constitutes a base of the band, and the pressure cuff 21 as a pressing member attached along the inner peripheral surface of the band-like body 23. The band-like body 23 is made of a resin material (silicone resin in this example). In this example, the band-like body 23 has flexibility in a thickness direction Z shown in FIG. 4 and is substantially non-stretchable so as to hardly stretch in a circumferential direction X.

In this example, the pressure cuff 21 is composed of a fluid bag prepared by causing two stretchable polyurethane sheets to face each other in the thickness direction Z and welding their peripheral edges together.

In addition, in this example, as shown in FIG. 1, the pressure cuff 21 is installed on a central part of the inner peripheral surface of the band-like body 23 in the width direction (Y direction), in which a dimension of the pressure cuff 21 in the width direction is set to 25 mm, smaller than the width dimension (35 mm to 40 mm) of the band-like body 23.

On the inner peripheral surface of the band-like body 23 of the band 20, a pair of protrusions 20g and 20h are integrally formed at positions facing each other across the pressure cuff 21 in the width direction (Y direction). The antenna substrates 41 and 42 are respectively installed on top of the protrusions 20g and 20h. Height dimensions of the protrusions 20g and 20h are set so that, for example, as shown in FIG. 5, upper surfaces of the antenna substrates 41 and 42 abut against the skin surface of the left wrist 90 with an appropriate contact pressure in a state in which the pressure cuff 21 is not pressurized. In addition, the positions of the protrusions 20g and 20h in the circumferential direction X of the band-like body 23 are set so that, when the sphygmomanometer 1 is correctly worn on the left wrist 90, the antenna substrates 41 and 42 correspond to the position of the radial artery 91. The protrusions 20g and 20h may be attached separately to the band-like body 23. An adhesive, for example, is used as an attachment means.

The antenna substrate 41 is, for example, formed by printing a conductive pattern of metal constituting a transmitting antenna 411 and a receiving antenna 412 on an upper surface of a dielectric substrate made of epoxy resin. Similarly, the antenna substrate 42 is, for example, formed by printing a conductive pattern made of metal constituting a transmitting antenna 421 and a receiving antenna 422 on an upper surface of a dielectric substrate made of epoxy resin.

The transmitting antennas 411 and 421 and the receiving antennas 412 and 422 are all composed of patch antennas and disposed at regular intervals in the circumferential direction X of the band 20. In this example, the transmitting antennas 411 and 421 and the receiving antennas 412 and 422 each have a square shape of 3 mm in length and width. In this example, a distance between the transmitting antenna 411 and the receiving antenna 412 and a distance between the transmitting antenna 421 and the receiving antenna 422 are set so that a distance between the centers thereof falls within a range of 8 mm to 10 mm in the circumferential direction X of the band 20.

In addition, in the width direction Y of the band 20, a distance between the pair of the transmitting antenna 411 and the receiving antenna 412 and the pair of the transmitting antenna 421 and the receiving antenna 422 is set to 30 mm in this example, slightly longer than the width (25 mm) of the pressure cuff 21. As the distance between the pair of the transmitting antenna 411 and the receiving antenna 412 and the pair of the transmitting antenna 421 and the receiving antenna 422, an optimal length may be appropriately selected according to the size of the sphygmomanometer 1 or the width of the pressure cuff 21 or the like.

Further, the control circuit board 43 is installed between the inner peripheral surface of the band-like body 23 of the band 20 and the pressure cuff 21, as shown in FIG. 3. The control circuit board 43 is formed by forming two pairs of a transmitting circuit and a receiving circuit on a printed wiring board composed of a dielectric. One pair of the transmitting circuit and the receiving circuit is connected to the transmitting antenna 411 and the receiving antenna 412 via a signal line (not shown). The other pair of the transmitting circuit and the receiving circuit is electrically connected to the transmitting antenna 421 and the receiving antenna 422 via the signal line. Each of the above transmitting circuits and receiving circuits is generally composed of an integrated circuit, but may also be a discrete circuit.

Figure 6:
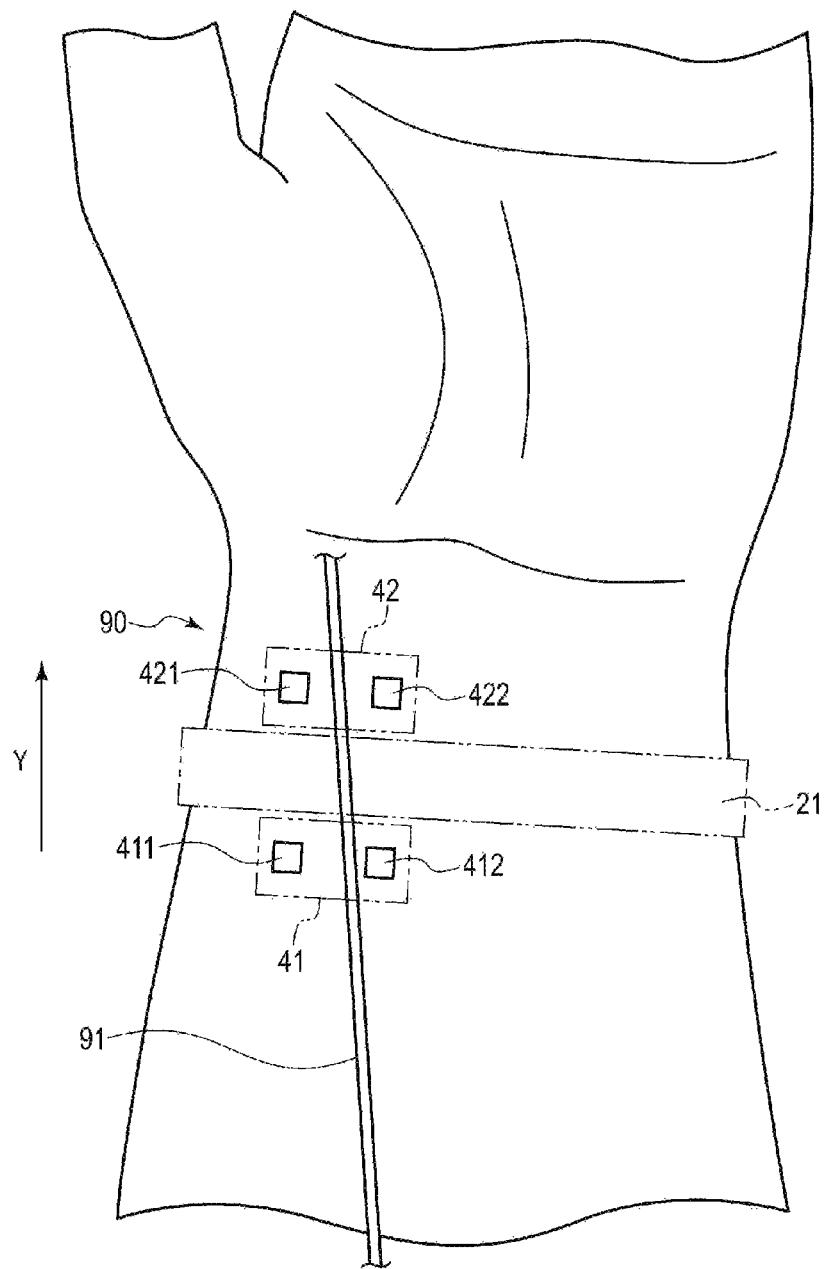
FIG. 6 is a plan view showing disposition positions of the antenna substrate and the pressure cuff with respect to the wrist when the biological information measuring device shown in FIG. 1 is worn on the left wrist.

FIG. 6 is a plan view illustrating the disposition positions of the pair of the transmitting antenna 411 and the receiving antenna 412 and the pair of the transmitting antenna 421 and the receiving antenna 422 with respect to the radial artery 91 together with the disposition position of the pressure cuff 21 when the sphygmomanometer 1 is worn on the left wrist 90 of the user.

As shown in FIG. 6, the transmitting and receiving antenna pair 421, 422 and the transmitting and receiving antenna pair 421, 422 are disposed at a predetermined distance (30 mm in this example) from each other along the longitudinal direction Y of the radial artery 91. In addition, the transmitting and receiving antenna pair 421, 422 and the transmitting and receiving antenna pair 421, 422 are each desired to be disposed so that the radial artery 91 is located between the transmitting antenna 411 and the receiving antenna 412 and between the transmitting antenna 421 and the receiving antenna 422.

(2) Configuration Example of Circuit System of Sphygmomanometer 1

(2-1) Overall Circuit Configuration

Figure 7:
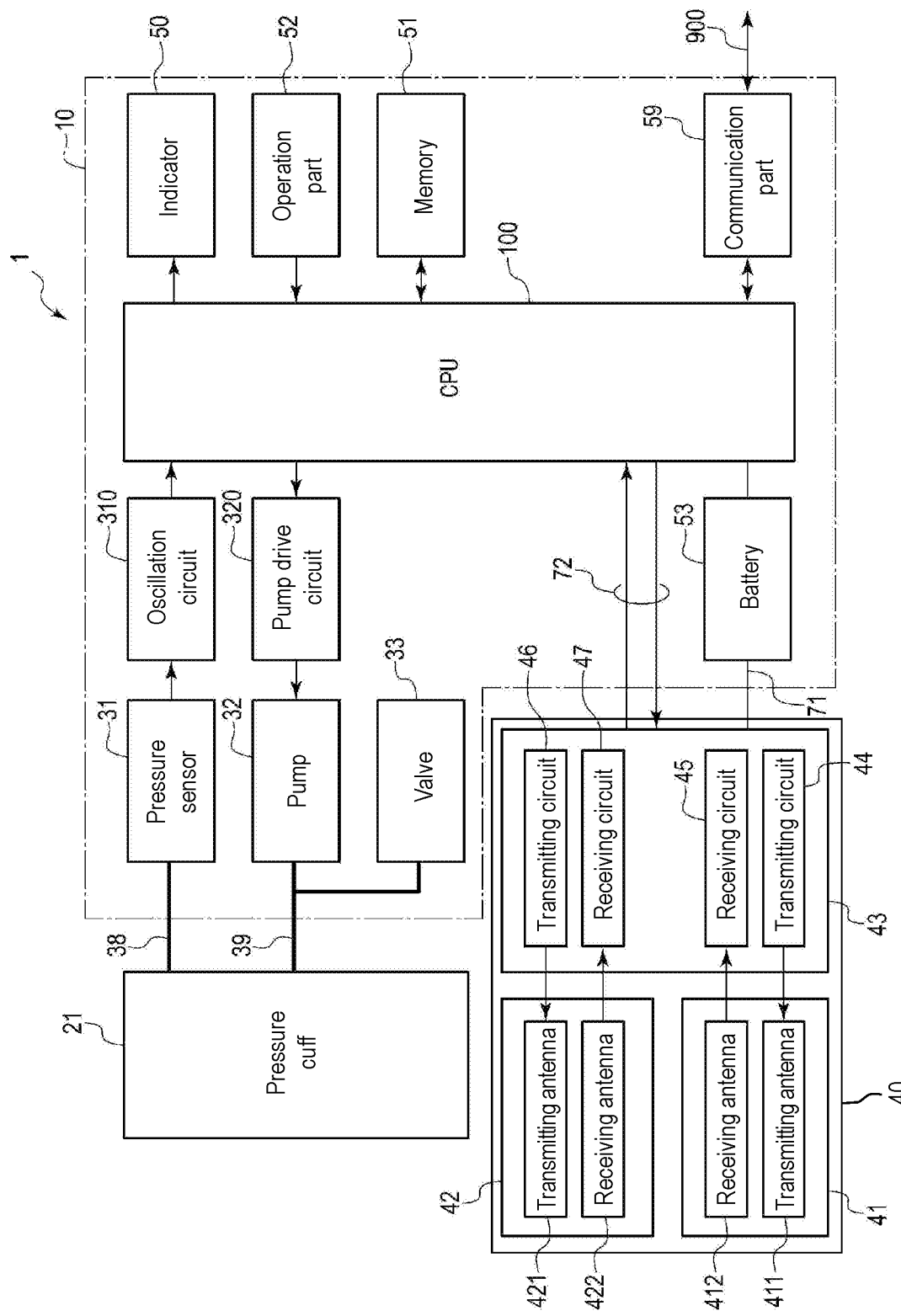
FIG. 7 is a block view showing an overall configuration of a control system of the biological information measuring device shown in FIG. 1.

FIG. 7 is a block view illustrating an overall configuration of a control system of the sphygmomanometer 1.

Provided in the main body 10 of the sphygmomanometer 1 are, in addition to the aforesaid indicator 50 and operation part 52, a hardware processor operating as a controller such as a central processing unit (CPU) 100 or the like, a memory 51 as a memory part, a communication part 59, a pressure sensor 31, a pump 32, a valve 33, an oscillation circuit 310 converting an output from the pressure sensor 31 into a frequency, and a pump drive circuit 320 driving the pump 32. 53 denotes a battery outputting a power supply voltage.

The aforesaid control circuit board 43 is connected to the CPU 100 via an interface circuit (not shown).

In this example, the indicator 50 is composed of an organic EL (electro luminescence) display, and displays information about the blood pressure measurement such as a blood pressure measurement result or the like and other information in accordance with display data output from the CPU 100. Moreover, the indicator 50 is not limited to the organic EL display, and may be an indicator of other type, for example, a liquid crystal display (LCD).

In this example, the operation part 52 is composed of a push-type switch, and inputs to the CPU 100 an operation signal corresponding to an instruction to start or stop the blood pressure measurement from the user. Moreover, the operation part 52 is not limited to the push-type switch, and may be, for example, a pressure-sensitive (resistive) or proximity (electrostatic capacitance) type touch panel switch. In addition, a microphone (not shown) may be provided to input the instruction to start the blood pressure measurement by the user's voice. Further, the operation part 52 is not essential, and it is also possible that the CPU 100 is configured to automatically generate an instruction to start the blood pressure measurement or an instruction to stop the blood pressure measurement in response to, for example, a start signal or the like output from a timer, which will be described later.

The memory 51 uses an HDD (hard disk drive), SSD (solid state drive), ROM, RAM or the like as a memory medium, and stores programs for controlling the sphygmomanometer 1, control data used to control the sphygmomanometer 1, setting data for setting various functions of the sphygmomanometer 1, detection signals of pressure or pulse wave, data representing a blood pressure measurement result, and so on. The memory 51 is also used as a work memory or the like when a program is executed.

The CPU 100 executes various functions as a controller in accordance with the programs stored in the memory 51.

For example, in the case of executing control for estimating the blood pressure by PTT, the CPU 100 gives an instruction to start transmission of a radio wave (measurement signal) to the transmitting circuits 44 and 46 of the control circuit board 43. Then, a reception signal corresponding to a reflected wave of the measurement signal from the radial artery 91 is captured from the receiving circuits 45 and 47, a pulse wave signal is detected from the reception signal, and PTT is calculated based on this pulse wave signal. Then, based on the calculated PTT value and the PTT-blood pressure relationship stored in the memory 51, a blood pressure value is estimated, and it is determined whether the estimated blood pressure value exceeds a range defined by a predetermined threshold.

In the case of executing the blood pressure measurement by the oscillometric method, for example, when it is determined that the above blood pressure estimate obtained by PTT has exceeded the range defined by the threshold, or in response to an input of the instruction from the operation part 52 to start blood pressure measurement, the CPU 100 performs control for driving the pump 32 (and the valve 33) based on a pressure detection signal output from the pressure sensor 31. In addition, in this example, the CPU 100 performs control for calculating the blood pressure value based on the pressure detection signal output from the pressure sensor 31.

The communication part 59 may transmit information including the blood pressure measurement result calculated by the CPU 100 to an external terminal device via a network 900, or may receive information from the external terminal device via the network 900 and pass it to the CPU 100. The communication via the network 900 may be wireless or wired. In this embodiment, the network 900 is the Internet, but is not limited thereto, and may be a network of other type, such as in-hospital LAN (local area network), or may be one-to-one communication using a USB cable or the like. The communication part 59 may include a micro USB connector.

The pump 32 and the valve 33 are connected to the pressure cuff 21 via an air pipe 39, and the pressure sensor 31 is connected to the pressure cuff 21 via an air pipe 38. The air pipes 39 and 38 may also be a single common pipe. The pressure sensor 31 detects the pressure in the pressure cuff 21 via the air pipe 38. The pump 32 is a piezoelectric pump in this example, and supplies air as a pressurizing fluid to the pressure cuff 21 through the air pipe 39 in order to increase the pressure (cuff pressure) in the pressure cuff 21. The valve 33 is mounted on the pump 32, and is configured to be controlled to open or close as the pump 32 is turned on or off.

That is, when the pump 32 is turned on, the valve 33 closes and seals the air in the pressure cuff 21; on the other hand, when the pump 32 is turned off, the valve 33 opens and discharges the air in the pressure cuff 21 into the atmosphere through the air pipe 39. Moreover, the valve 33 has a function of a check valve, and the discharged air will not flow backward. The pump drive circuit 320 drives the pump 32 based on a control signal given from the CPU 100.

The pressure sensor 31 is a piezoresistive pressure sensor in this example, detecting the pressure (in this example, the pressure with the atmospheric pressure as a reference (zero)) of the band 20 (pressure cuff 21) through the air pipe 38, and outputting it as a time-series signal. The oscillation circuit 310 oscillates based on an electric signal value from the pressure sensor 31 that is based on a change in electric resistance due to a piezoresistive effect, and outputs a frequency signal having a frequency corresponding to the electric signal value of the pressure sensor 31 to the CPU 100. In this example, the output of the pressure sensor 31 is used to control the pressure of the pressure cuff 21, and to calculate a blood pressure value (including systolic blood pressure (SBP) and diastolic blood pressure (DBP)) by the oscillometric method.

The battery 53 supplies power to an element (in this example, each of the CPU 100, the pressure sensor 31, the pump 32, the valve 33, the indicator 50, the memory 51, the communication part 59, the oscillation circuit 310, and the pump drive circuit 320) mounted on the main body 10. The battery 53 also supplies power to the transmitting circuits 44 and 46 and the receiving circuits 45 and 47 of the control circuit board 43 through a feed line 71. The feed line 71, together with signal wiring 72, extends and is provided between the main body 10 and a transmitting and receiving part 40 along the circumferential direction X of the band 20 while being sandwiched between the band-like body 23 of the band 20 and the pressure cuff 21.

(2-2) Configuration of Blood Pressure Estimation Part Based on Pulse Transit Time (PTT)

Figure 8:
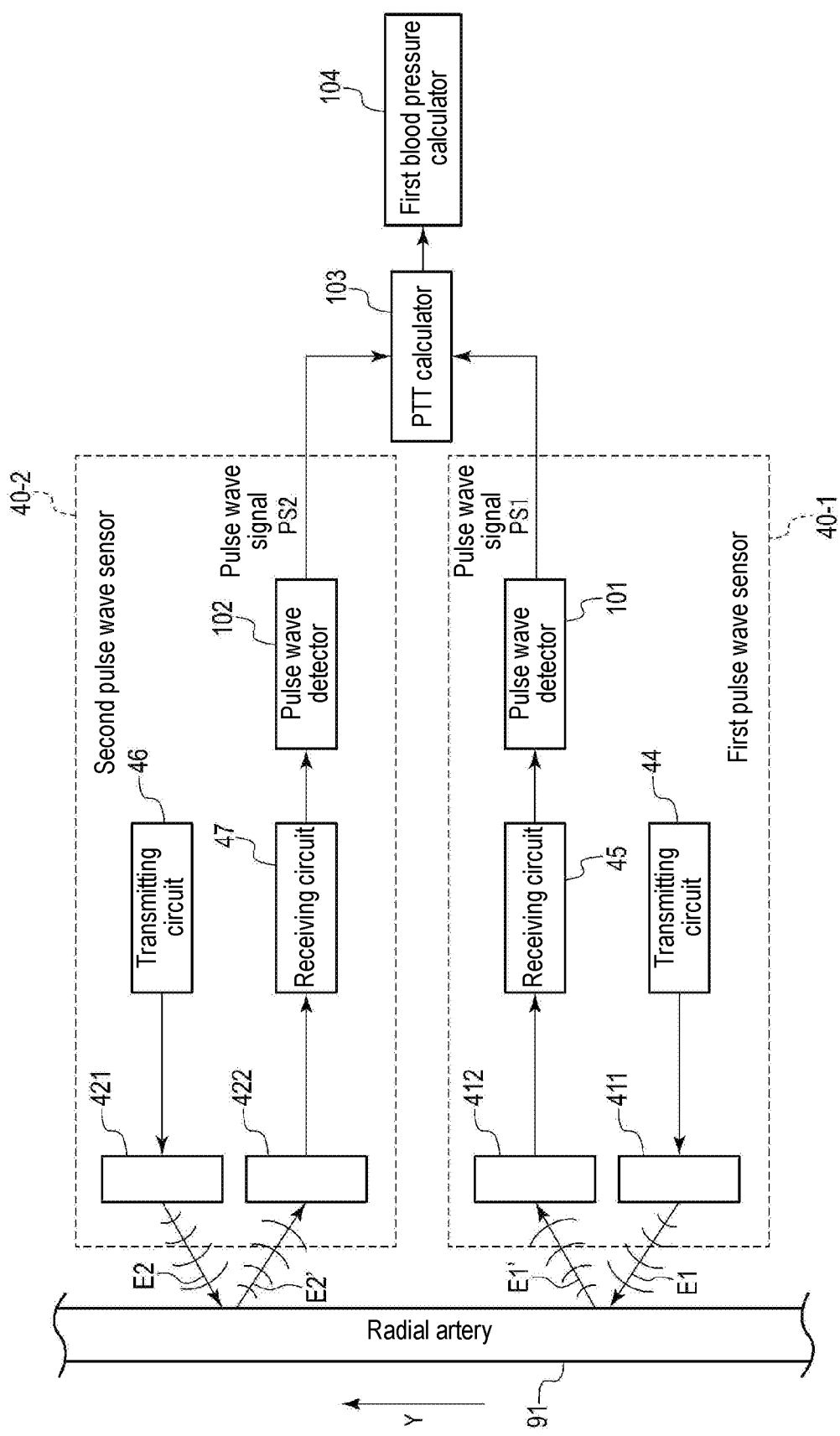
FIG. 8 is a block view showing a configuration of a pulse wave sensor in the control system shown in FIG. 7.

FIG. 8 is a block view illustrating configurations of a first pulse wave sensor 40-1 and a second pulse wave sensor 40-2.

As described above, the control circuit board 43 is provided with two transmitting and receiving circuits, that is, the transmitting circuit 44 and the receiving circuit 45, and the transmitting circuit 46 and the receiving circuit 47. The transmitting circuit 44 and the receiving circuit 45 are respectively connected to the transmitting antenna 411 and the receiving antenna 412 provided on the antenna substrate 41 via signal lines connecting the control circuit substrate 43 and the antenna substrate 41. Similarly, the transmitting circuit 46 and the receiving circuit 47 are respectively connected to the transmitting antenna 421 and the receiving antenna 422 provided on the antenna substrate 42 via signal lines connecting the control circuit substrate 43 and the antenna substrate 42.

The first pulse wave sensor 40-1 is composed of the transmitting antenna 411 and the receiving antenna 412 of the antenna substrate 41, the transmitting circuit 44 and the receiving circuit 45 respectively connected to the transmitting antenna 411 and the receiving antenna 412, and a pulse wave detector 101. The second pulse wave sensor 40-2 is composed of the transmitting antenna 421 and the receiving antenna 422 of the antenna substrate 42, the transmitting circuit 46 and the receiving circuit 47 respectively connected to the transmitting antenna 421 and the receiving antenna 422, and a pulse wave detector 102.

In response to a transmission instruction from the CPU 100, the transmitting circuits 44 and 46 supply the measurement signal to the transmitting antennas 411 and 421 to which they are respectively connected, and transmit radio waves E1 and E2 toward the left wrist 90 (more accurately, the corresponding portion of the radial artery 91) as the measured part. In this example, radio waves having a frequency in the 24 GHz band are used as the radio waves E1 and E2.

The receiving circuits 45 and 47 respectively receive reflected waves E1' and E2' of the radio waves E1 and E2 from the radial artery 91 via the receiving antennas 412 and 422, detect and amplify the same, and output reception signals thereof to the CPU 100.

The pulse wave detectors 101 and 102 respectively convert the reception signals output from the receiving circuits 45 and 47 into digital signals by an A/D converter (not shown), capture the digital signals, detect pulse wave signals PS1 and PS2 representing a pulsation waveform of the radial artery 91, and output them to a PTT calculator 103.

The PTT calculator 103 calculates a time difference between the pulse wave signals PS1 and PS2 output from the pulse wave detectors 101 and 102 as a pulse transit time (PTT), and outputs the calculated pulse transit time (PTT) to a first blood pressure calculator 104. The first blood pressure calculator 104 reads the preset PTT-blood pressure relationship from the memory 51, and estimates a blood pressure value corresponding to the calculated pulse transit time (PTT) in accordance with the relationship.

Here, the pulse wave detectors 101 and 102, the PTT calculator 103, and the first blood pressure calculator 104 are all realized by the CPU 100 executing a predetermined program.

(2-3) Configuration of Blood Pressure Measuring Part Using Oscillometric Method

Figure 9:
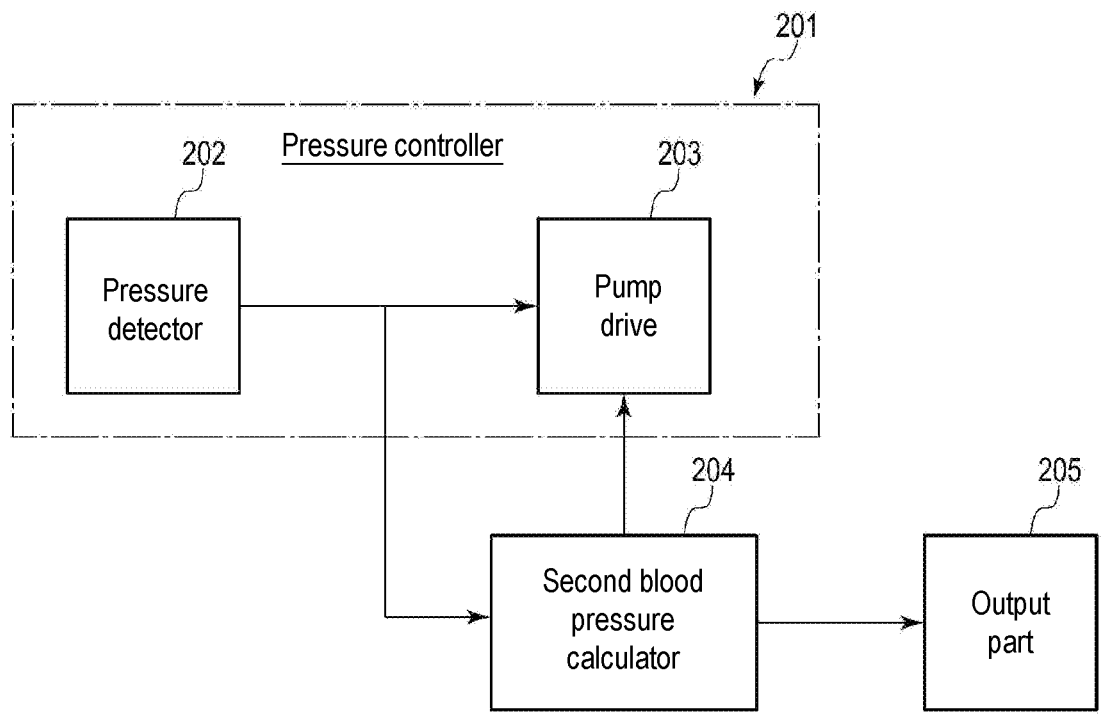
FIG. 9 is a block view showing a configuration of a blood pressure measurement system by an oscillometric method in the control system shown in FIG. 7.

FIG. 9 is a block view illustrating a configuration of a blood pressure measuring part using the oscillometric method.

The blood pressure measuring part using the oscillometric method includes a pressure controller 201, a second blood pressure calculator 204, and an output part 205. These functional units are all realized by causing the CPU 100 to execute a program.

The pressure controller 201 has a pressure detector 202 and a pump drive 203. The pressure detector 202 processes the frequency signal input from the pressure sensor 31 through the oscillation circuit 310 and performs processing for detecting the pressure (cuff pressure) in the pressure cuff 21. Based on the detected cuff pressure, the pump drive 203 performs processing for driving the pump 32 and the valve 33 through the pump drive circuit 320. Accordingly, the pressure controller 201 supplies air to the pressure cuff 21 at a predetermined pressurization rate and controls the pressure.

The second blood pressure calculator 204 obtains a variation component of arterial volume included in the cuff pressure as a pulse wave signal, and performs processing for calculating the blood pressure value (systolic blood pressure SBP and diastolic blood pressure DBP) by applying a known algorithm by the oscillometric method based on the obtained pulse wave signal. When the calculation of the blood pressure value is completed, the second blood pressure calculator 204 stops the processing of the pump drive 203.

The output part 205 performs processing for displaying the calculated blood pressure value (systolic blood pressure SBP and diastolic blood pressure DBP) on the indicator 50 in this example.

(Operation Example)

Figure 10:
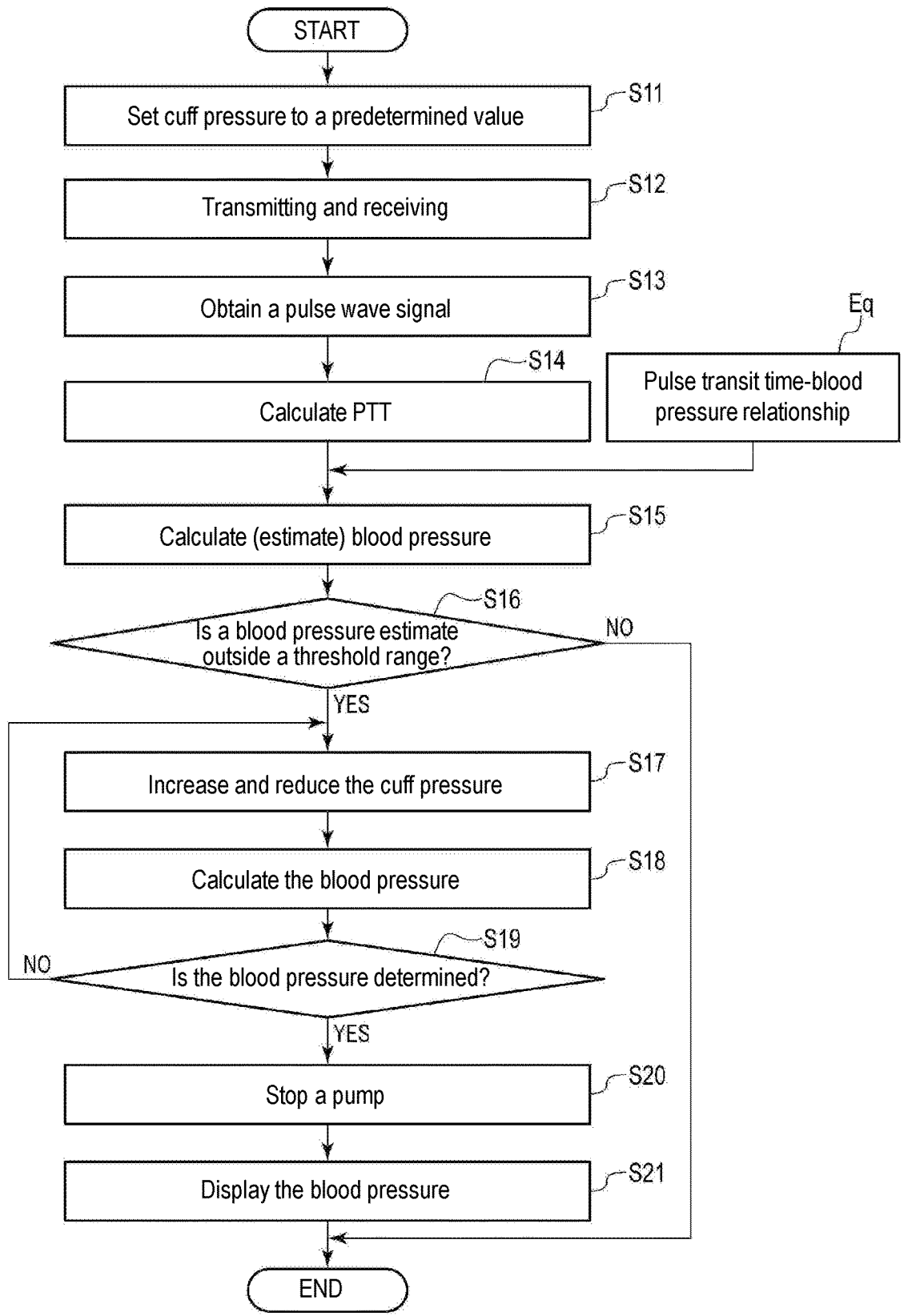
FIG. 10 is a flowchart showing one example of a control procedure and control content by the control system of the biological information measuring device shown in FIG. 1.

Next, an operation example of the sphygmomanometer 1 configured as above is described. FIG. 10 is a flowchart illustrating a control procedure and control content by the CPU 100. Here, the sphygmomanometer 1 is described as being worn on the left wrist 90 of the user by the aforesaid wearing procedure.

(1) Blood Pressure Estimation by Pulse Transit Time (PTT)

When the user gives an instruction to measure the blood pressure based on PTT by a push-type switch as the operation part 52 provided on the main body 10, the CPU 100 executes a control operation as follows. It is also possible that the above instruction to start the PTT-based blood pressure measurement is configured to be automatically generated by the CPU 100 in response to, for example, a start signal or the like output from a timer.

That is, first, in step S11, the CPU 100 closes the valve 33, performs control for driving the pump 32 via the pump drive circuit 320 and sending air to the pressure cuff 21, and pressurizes the pressure cuff 21 to a predetermined value. In this example, the pressure is set to the extent that the wearing position of the sphygmomanometer 1 does not shift during the user's activity, that is, the pressure is set to a low pressure (for example, about 5 mmHg) to the extent that the user does not feel discomfort and a contact position of a transmitting and receiving antenna pair with respect to a measured part does not shift.

In one embodiment, as described above, on the inner peripheral surface of the band-like body 23 constituting the base of the band 20, the protrusions 20g and 20h set to an appropriate height are formed, and the antenna substrates 41 and 42 are installed on the protrusions 20g and 20h. Hence, it is possible for the transmitting antennas 411 and 421 and the receiving antennas 412 and 422 to abut against the skin surface of the measured part of the user with an appropriate pressure. Hence, step S11 can also be omitted.

In this state, the CPU 100 instructs the control circuit board 43 to start transmission of a measurement signal in step S12. When the above instruction is received, the measurement signal is supplied from the transmitting circuits 44 and 46 to the transmitting antennas 411 and 421 in a preset cycle. As a result, for example, as shown in (A) of FIG. 11, the transmitting antennas 411 and 421 transmit the radio waves E1 and E2 corresponding to the measurement signal to the measured part 90. The measurement signal may be generated from the transmitting circuits 44 and 46 at irregular time intervals, or may be generated continuously.

Figure 11:
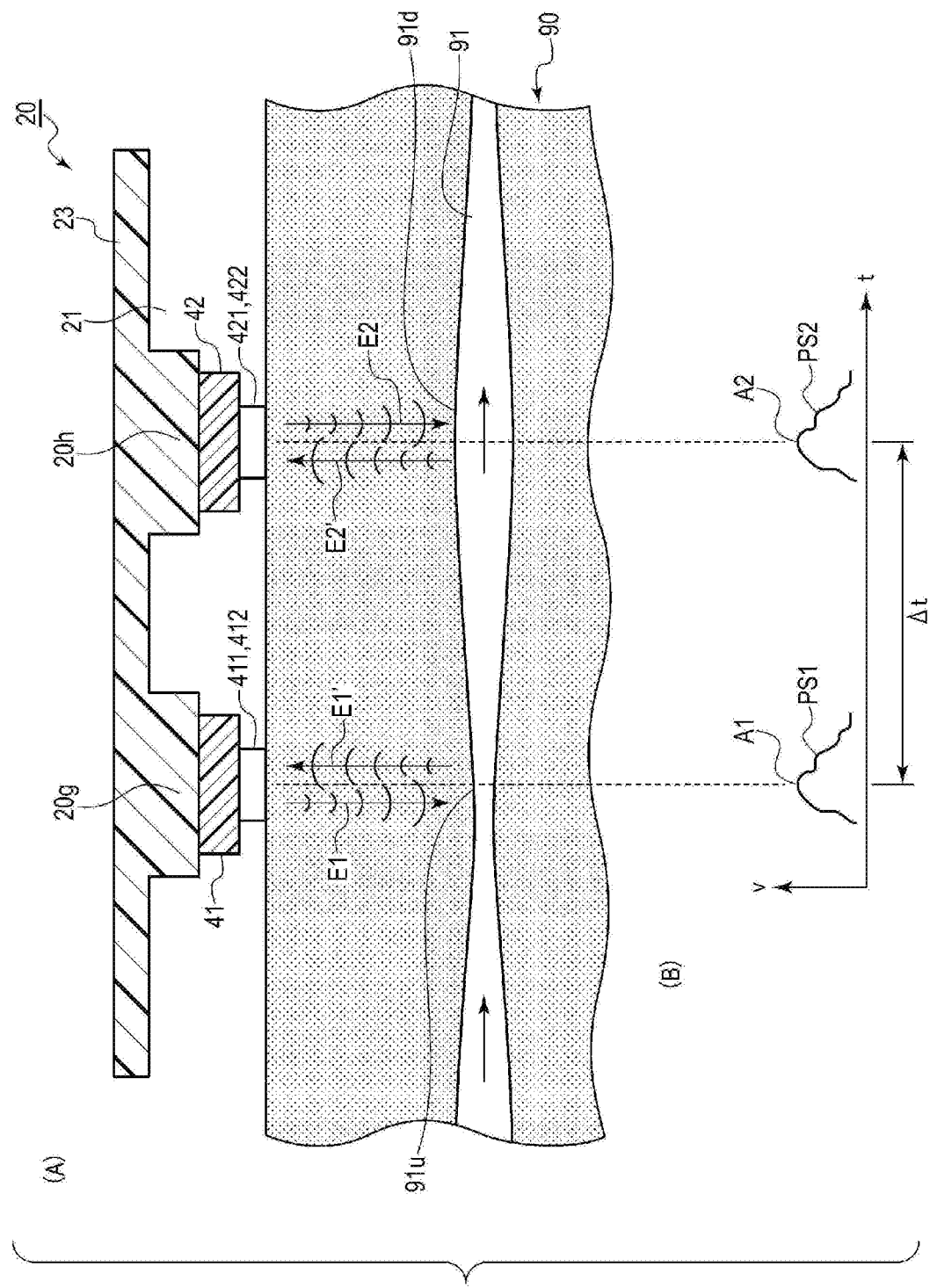
FIG. 11 is a diagram for describing a pulse wave measurement operation, in which (A) schematically shows a section of the left wrist along a longitudinal direction, and (B) is a diagram showing one example of waveforms of pulse waves obtained by a first and second pulse wave sensor.

Then, for example, as shown in (A) of FIG. 11, the reflected waves E1' and E2' of the radio waves E1 and E2 from the radial artery 91 in the measured part 90 are received by the receiving antennas 412 and 422 respectively paired with the transmitting antennas 411 and 421, and reception signals thereof are detected and amplified in the receiving circuits 45 and 47 and output to the CPU 100.

The CPU 100 captures the reception signals for the reflected waves E1' and E2' that are output from the receiving circuits 45 and 47, and detects the pulse wave signals PS1 and PS2 respectively as follows in step S13. (B) of FIG. 11 is a diagram showing a detection example of the pulse wave signals PS1 and PS2.

That is, the CPU 100 acts as the pulse wave detector 101, detecting the pulse wave signal PS1 representing a pulse wave of an upstream portion 91u of the radial artery 91 from outputs of the receiving circuit 45 during vasodilation and during vasoconstriction. In addition, the CPU 100 acts as the pulse wave detector 102, detecting the pulse wave signal PS2 representing a pulse wave of a downstream portion 91d of the radial artery 91 from outputs of the receiving circuit 47 during vasodilation and during vasoconstriction.

The above operations are described in more detail. That is, in the state in which the sphygmomanometer 1 is worn, as shown in (A) of FIG. 11, in the longitudinal direction (corresponding to the width direction Y of the band 20) of the left wrist 90, the transmitting and receiving antenna pair 411, 412 faces the upstream portion 91u of the radial artery 91 passing through the left wrist 90. On the other hand, the transmitting and receiving antenna pair 421, 422 faces the downstream portion 91d of the radial artery 91. A signal detected by the transmitting and receiving antenna pair 411, 412 represents a change in a distance between the upstream portion 91u of the radial artery 91 and the transmitting and receiving antenna pair 411, 412 associated with a pulse wave (which causes widening and narrowing of a blood vessel). Similarly, a signal detected by the transmitting and receiving antenna pair 421, 422 represents a change in a distance between the downstream portion 91d of the radial artery 91 and the transmitting and receiving antenna pair 421, 422 associated with a pulse wave. Based on the signals output from the receiving circuits 45 and 47, the pulse wave detector 101 of the first pulse wave sensor 40-1 and the pulse wave detector 102 of the second pulse wave sensor 40-2 respectively output, in time series, the pulse wave signal PS1 and the pulse wave signal PS2 each having a mountain-shaped waveform as shown in (B) of FIG. 11.

In this example, a reception level of the receiving antennas 412 and 422 is about 1μW (-30 dBm in decibel value for 1 mW). An output level of the receiving circuits 45 and 47 is about 1 volt. Peaks A1 and A2 of the pulse wave signal PS1 and the pulse wave signal PS2 respectively are about 100 mV to 1 volt.

Next, in step S14, the CPU 100 acts as the PTT calculator 103, calculating the time difference between the pulse wave signal PS1 and the pulse wave signal PS2 as the pulse transit time (PTT). More specifically, in this example, a time difference Δt between the peak A1 of the pulse wave signal PS1 and the peak A2 of the pulse wave signal PS2 shown in (B) of FIG. 11 is calculated as the pulse transit time (PTT). The pulse transit time (PTT) is not limited to the time difference Δt between the peaks of the pulse wave signals PS1 and PS2, and may be calculated as a time difference between rising timings of the respective waveforms of the pulse wave signals PS1 and PS2.

Subsequently, in step S15, the CPU 100 acts as the first blood pressure calculator 104, reading from the memory 51 a relationship (also called a correspondence equation) Eq between the pulse transit time (PTT) and the blood pressure. Then, based on the correspondence equation Eq and the pulse transit time (PTT) calculated in step S14, a blood pressure estimate is calculated. Here, when the pulse transit time is represented by DT and the blood pressure is represented by EBP, the correspondence equation Eq between the pulse transit time (PTT) and the blood pressure is, for example, provided as a known fractional function including a term 1/DT2, as shown by:

$$EBP = \alpha/DT2 + \beta \quad \text{(Eq. 1)}$$

(however, α and β each represent a known coefficient or constant). This correspondence equation is described in detail, for example, in Japanese Patent Laid-Open No. H10-201724.

Moreover, as the correspondence equation Eq between the pulse transit time and the blood pressure, other known correspondence equations such as an equation including a term 1/DT and a term DT in addition to the term 1/DT2, like:

$$EBP = \alpha/DT2 + \beta/DT + \gamma DT + \delta \quad \text{(Eq. 2)}$$

(however, α, β, γ and δ each represent a known coefficient or constant), can be used.

When a blood pressure value is estimated by PTT as described above, next, in step S16, the CPU 100 compares the above blood pressure estimate with a preset threshold representing a normal range of the blood pressure, and determines whether the blood pressure estimate is outside the range indicated by the threshold. Then, if the blood pressure estimate is within the range indicated by the threshold, the above control by step S12 is repeated until the operation part 52 inputs an instruction to end the blood pressure measurement by PTT.

(2) Blood Pressure Measurement Using Oscillometric Method

When it is determined in step S16 that the above blood pressure estimate is outside the range indicated by the threshold, the CPU 100 executes blood pressure measurement control using an oscillometric method as follows.

That is, the CPU 100 first turns off the pump 32 via the pump drive circuit 320, opens the valve 33, and exhausts the air in the pressure cuff 21. Subsequently, control for setting the current output value of the pressure sensor 31 as a value corresponding to atmospheric pressure is performed (adjustment to 0 mmHg).

Subsequently, in step S17, the CPU 100 acts as the pump drive 203 of the pressure controller 201, closing the valve 33, and then performing the control for driving the pump 32 via the pump drive circuit 320 and sending air to the pressure cuff 21. Accordingly, as the pressure cuff 21 is inflated, the cuff pressure is gradually increased, and the left wrist 90 as the measured part is gradually pressed.

In this pressurization process, in order to calculate the blood pressure value, the CPU 100 acts as the pressure detector 202 of the pressure controller 201, monitoring the cuff pressure by the pressure sensor 31, and detecting, as a pulse wave signal, a variation component of arterial volume generated in the radial artery 91 of the left wrist 90.

Next, in step S18, the CPU 100 acts as the second blood pressure calculator 204, attempting to calculate the blood pressure value (systolic blood pressure SBP and diastolic blood pressure DBP) by applying a known algorithm by the oscillometric method based on the pulse wave signal detected at this time. Then, it is determined in step S19 whether the blood pressure value has been calculated.

At this time, if the blood pressure value still has not been calculated due to lack of data, the processings of steps S17 to S19 are repeated as long as the cuff pressure has not reached an upper limit pressure (which is predetermined to be, for example, 300 mmHg, for safety).

On the other hand, assuming that the blood pressure value has been calculated, then, in step S20, the CPU 100 stops the pump 32, opens the valve 33, and performs control for exhausting the air in the pressure cuff 21. Finally, in step S21, the CPU 100 acts as the output part 205, displaying a measurement result of the blood pressure value on the indicator 50 and storing the measurement result in the memory 51.

The blood pressure value calculation processing may not necessarily be performed in the pressurization process but may be performed in a depressurization process. In addition, the measurement result of the blood pressure value may only be stored in the memory 51 without being displayed on the indicator 50; further, it may be transmitted from the communication part 59 to a pre-associated user terminal such as a smartphone or the like so as to be displayed on the user terminal. Further, data representing the blood pressure measurement result may be transferred from the communication part 59 or the smartphone to a terminal of a family member or a doctor.

The above description has described, as an example, a case where the blood pressure measurement operation by the oscillometric method is performed when a blood pressure estimate by PTT exceeds the range defined by the threshold. However, in one embodiment, the blood pressure estimation operation by PTT and the blood pressure measurement operation using the oscillometric method can also be respectively independently performed according to the operation of the operation part.

(Effects of One Embodiment)

As described in detail above, in one embodiment of the present invention, in the sphygmomanometer 1 worn on the left wrist 90 of the subject (user) for use, on the inner peripheral surface of the band-like body 23 constituting the base of the band 20, the portion for installing the pressure cuff 21 and the protrusions 20g and 20h for installing the antenna substrates 41 and 42 are separately provided, and the pressure cuff 21 and the antenna substrates 41 and 42 are respectively installed on these portions.

Thus, the antenna substrates 41 and 42 are installed on the protrusions 20g and 20h formed on the band-like body 23 of the band 20, instead of on the pressing surface of the pressure cuff 21. Hence, even if the pressurization and depressurization of the pressure cuff 21 are repeated, there is no longer a concern that a deterioration of the installation state, such as deformation or falling or the like, may occur in the antenna substrates 41 and 42. Accordingly, it is possible to maintain high structural reliability of the sphygmomanometer 1.

In addition, in the state in which the sphygmomanometer 1 is worn on the measured part 90 of the user, the antenna substrates 41 and 42 contact the skin of the measured part 90 independently of the pressure cuff 21. Hence, when the pressure cuff 21 is pressurized, the antenna substrates 41 and 42 are no longer pressed against the skin surface by the pressure of the pressure cuff 21. Thus, the concern that the user may feel discomfort such as pain on the skin or the like is reduced, and the usability of the sphygmomanometer 1 can be maintained high.

Further, since the height dimension of the protrusions 20g and 20h formed on the band-like body 23 of the band 20 is set according to the thickness dimension of the pressure cuff 21 during non-pressurization, it is possible to bring the antenna substrates 41 and 42 into contact with the skin surface of the subject with an appropriate pressure during the blood pressure estimation operation by PTT. As a result, attenuation of the radio wave is suppressed, mixing of disturbance is reduced, and the S/N of the pulse wave signal can be maintained high.

[Modifications]

(1) In the one embodiment mentioned above, a case has been described as an example where two antenna substrates 41 and 42 each provided with a transmitting and receiving antenna pair are installed in the width direction Y of the band 20, that is, in the longitudinal direction of the radial artery 91, and the blood pressure estimation by PTT is accordingly performed. However, the present invention is not limited to this configuration, and may be configured as follows. Only one antenna substrate provided with one transmitting and receiving antenna pair is provided, and a pulse wave of the radial artery 91 is accordingly detected at any one position in the radial artery 91.

Figure 12:
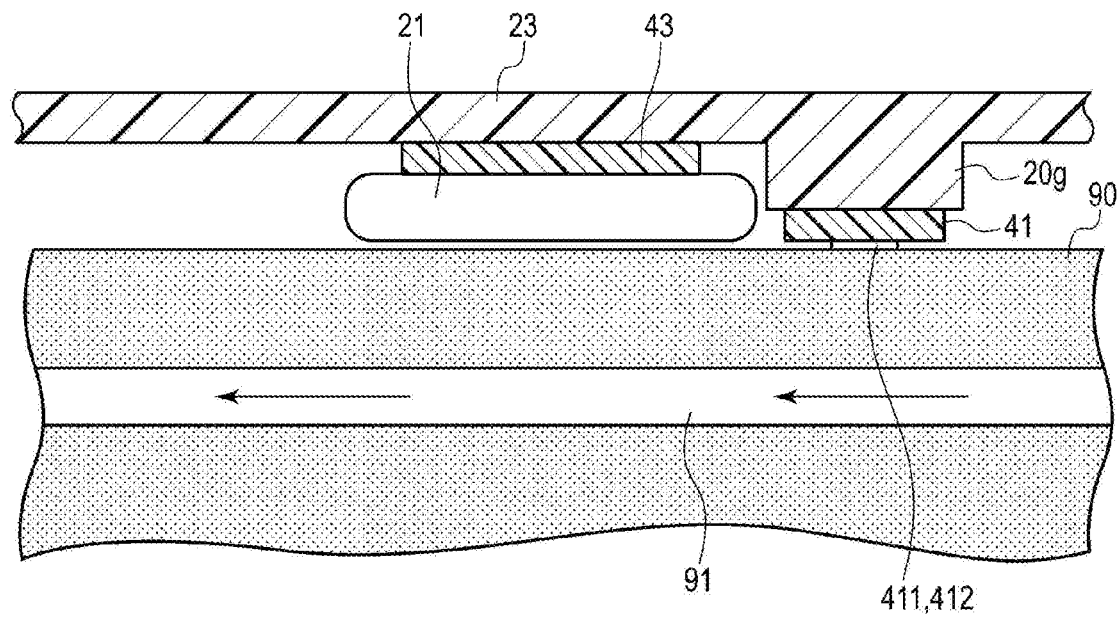
FIG. 12 is an enlarged cross-sectional view of a main part in a state in which a biological information measuring device according to Modification 1 of the present invention is worn on the left wrist.

FIG. 12 is a sectional view showing one example of the configuration. As shown in the figure, on the inner peripheral surface of the band-like body 23 of the band 20, one protrusion 20g is formed on one side of the position where the pressure cuff 21 is disposed, and the antenna substrate 41 is installed on the protrusion 20g. This configuration is same as the configuration of the one embodiment shown in FIG. 5 mentioned above in the point that the control circuit board 43 is disposed between the pressure cuff 21 and the band-like body 23.

According to the above configuration, the antenna substrate 41 is installed on the protrusion 20g formed on the band-like body 23 of the band 20, instead of on the pressing surface of the pressure cuff 21. Hence, even if the pressurization and depressurization of the pressure cuff 21 are repeated, there is no longer a concern that a deterioration of the installation state, such as deformation or falling or the like, may occur in the antenna substrate 41. Thus, the structural reliability of the sphygmomanometer 1 can be enhanced, and it becomes possible to measure a pulse wave with high quality and reliability.

In addition, in the state in which the sphygmomanometer 1 is worn on the measured part 90 of the user, the antenna substrate 41 contacts the skin of the measured part 90 independently of the pressure cuff 21. Hence, when the pressure cuff 21 is pressurized, the pressure thereof will not press the antenna substrate 41 against the skin surface. Accordingly, the concern that the user may feel discomfort such as pain on the skin or the like is reduced.

Figure 13:
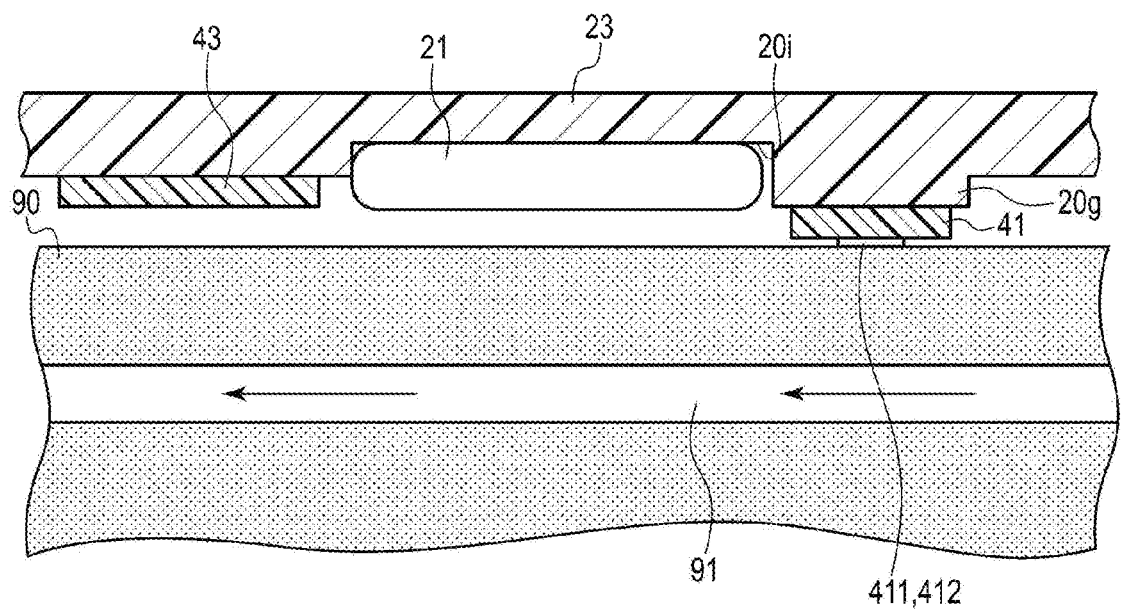
FIG. 13 is an enlarged cross-sectional view of a main part in a state in which a biological information measuring device according to Modification 2 of the present invention is worn on the left wrist.

(2) In the one embodiment mentioned above, a case has been described where only the protrusions 20g and 20h for installing the antenna substrates 41 and 42 are provided on the inner peripheral surface of the band-like body 23 of the band 20. However, the present invention is not limited thereto. For example, as shown in FIG. 13, a groove-shaped recess 20i may be formed on the inner peripheral surface of the band-like body 23 in the circumferential direction, and the pressure cuff 21 may be disposed in the recess 20i. With such a configuration, the pressure cuff 21 on which pressurization and depressurization are repeated can be more stably held. Accordingly, problems such as contact of the pressure cuff 21 with the antenna substrates 41 and 42 disposed adjacent thereto or the like can be prevented.

Moreover, the control circuit board 43 may be disposed, for example, in an empty space in the band-like body 23 of the band 20, that is, a position where the control circuit board 43 does not overlap the pressure cuff 21, as shown in FIG. 13, instead of being disposed between the pressure cuff 21 and the band-like body 23.

(3) In the one embodiment mentioned above, a case has been described as an example where the antenna substrates 41 and 42 are disposed at predetermined intervals along the longitudinal direction (Y direction) of the radial artery 91. However, the present invention is not limited thereto. A set of antenna substrates having the same configuration as the antenna substrates 41 and 42 may be disposed at predetermined intervals in a direction orthogonal to the radial artery 91, that is, in the circumferential direction (X direction) of the band 20. At this time, the above set of antenna substrates may be one set, or a plurality of sets may be disposed at predetermined intervals in the X direction.

Even when the number of the antenna substrate 41 is one as shown in FIG. 12, a plurality of antenna substrates 41 may be disposed at predetermined intervals in the direction (X direction) orthogonal to the radial artery 91.

With the above configuration, the transmission and reception of the measurement signal and the reflection signal are respectively performed at a plurality of positions in the direction orthogonal to the radial artery 91. Hence, for example, although the position of the radial artery 91 of the user differs from person to person, and even if the wearing position of the band 20 with respect to the measured part shifts in the X direction, it becomes possible to bring at least one of the plurality of antenna substrates close to the artery. Accordingly, it becomes possible to measure a pulse wave with good quality.

(4) The antenna substrates 41 and 42 and the control circuit board 43 may be composed of flexible boards. In this way, the band 20 can be made thinner. Further, it is possible that the antenna substrates 41 and 42 and the control circuit board 43 are composed of a single common flexible board. In addition, the antenna substrate may be covered or provided with a protective film made of a dielectric material for protecting the transmitting antenna and the receiving antenna. With such a configuration, an effect of further reducing the discomfort when the transmitting antenna and the receiving antenna come into contact with the user's skin can be expected to be achieved.

(5) In the one embodiment mentioned above, a case has been described as an example where a pulse wave signal, a pulse transit time and a blood pressure value are measured as biological information by the sphygmomanometer 1. However, the present invention is not limited thereto. Other information may be obtained from the pulse wave, such as that a pulse rate may be measured, or a waveform of the pulse wave may be analyzed to determine the user's cardiovascular state for performing identity authentication on the user, or the like.

(6) The biological information measuring device may include, in addition to the type worn on the wrist, the types worn on the other parts such as on other upper limb such as the upper arm or the like, or on a lower limb such as the thigh, the ankle or the like. In short, the biological information measuring device may be worn on any part as long as the part has an artery under the skin and can be pressurized by the pressure cuff.

(7) In the one embodiment mentioned above, a case has been described as an example where a series of processings, from the pressure measurement by the pulse wave and the pressure cuff to the blood pressure value calculation, are all performed in the sphygmomanometer 1. However, the biological information measuring device may be configured to only perform the pulse wave measurement, the pressurization and depressurization of the pressure cuff, and the pressure measurement operation in the above processes, directly or indirectly transmit each of the measured values to an external terminal such as a smartphone or a personal computer, a server computer or the like via, for example, a wireless network, a wired network, or a memory medium, and calculate a blood pressure value based on PTT and a blood pressure value based on the oscillometric method respectively in these external terminals.

(8) The transmitting and receiving antenna pair may be disposed in the longitudinal direction (Y direction) of the radial artery 91 instead of the direction (X direction) orthogonal to the longitudinal direction (Y direction) of the radial artery 91. In addition, patterns of the transmitting antenna and the receiving antenna may be in a linear shape or loop shape in addition to a rectangular shape. Further, the antenna support member for installing the transmitting antenna and the receiving antenna as well as the control circuit support member for installing the control circuit are not limited to the printed wiring boards, and may be, for example, simple members made of a resin material.

Regarding other items, such as the number of the antenna support member (transmitting and receiving antenna pair) installed or the installation positions and installation structures thereof, the procedure of the blood pressure measurement control by PTT and the oscillometric method, and the control content and so on, various modifications can be made and implemented without departing from the gist of the present invention.

The embodiment of the present invention has been described in detail as above. However, the above description is merely an example of the present invention in all respects. It goes without saying that various improvements or modifications can be made without departing from the scope of the present invention. That is, when implementing the present invention, a specific configuration corresponding to the embodiment may be appropriately adopted.

In short, the present invention is not limited to the above one embodiment or each modification as it is, and the constituent elements can be modified and embodied in the implementation stage without departing from the gist of the present invention. In addition, various inventions can be formed by appropriately combining a plurality of constituent elements disclosed in each of the above embodiments. For example, some of all the constituent elements shown in the embodiments may be deleted. Further, the constituent elements in different embodiments may be appropriately combined.

[Supplementary Note]

Some or all of the above embodiments may be described as in the following supplementary note in addition to the claims, but are not limited thereto.

(Supplementary Note 1)

A biological information measuring device, including:
a band-shaped band member (23), worn so as to surround a measured part (90) including an artery (91) of a living body;
a pressing member (21), disposed on a surface of the band member (23) that faces the measured part (90), expanding due to injection of a fluid during blood pressure measurement and pressing the measured part (90); and
at least one antenna support member (41), (42), installed on a portion of the surface of the band member (20) that faces the measured part (90), where the pressing member (21) is not disposed, in a state in which the band member (20) is worn on and is in contact with the measured part (90), wherein
the antenna support member (41), (42) has an antenna element (411), (412), (421), (422) transmitting a measurement signal composed of a radio wave to the measured part (90) and receiving a reflection signal of the measurement signal from the measured part (90).

What is claimed is:

1. A biological information measuring device, comprising:
    a band-shaped band member, configured to be worn so as to surround a measured part comprising an artery of a living body;
    a pressure cuff, disposed on a surface of the band member that faces the measured part, expanding due to injection of a fluid during blood pressure measurement and pressing the measured part; and
    at least one antenna substrate, installed on a portion of the surface of the band member that faces the measured part instead of being attached to a surface of the pressure cuff that faces the measured part, in a state in which the band member is worn on and is in contact with the measured part,
    wherein the at least one antenna substrate has an antenna element transmitting a measurement signal composed of a radio wave to the measured part and receiving a reflection signal of the measurement signal from the measured part.

2. The biological information measuring device according to claim 1, wherein a plurality of the at least one antenna substrate are disposed at predetermined intervals in a direction along the artery comprised in the measured part.

3. The biological information measuring device according to claim 1, wherein a plurality of the antenna are disposed on one antenna substrate at predetermined intervals in a direction along the artery comprised in the measured part.

4. The biological information measuring device according to claim 1, wherein a plurality of the at least one antenna substrate are disposed at predetermined intervals in a direction orthogonal to the artery comprised in the measured part.

5. The biological information measuring device according to claim 1, wherein a plurality of the antenna are disposed on one antenna substrate at predetermined intervals in a direction orthogonal to the artery comprised in the measured part.

6. The biological information measuring device according to claim 1, wherein
    the band member has, on the surface that faces the measured part, a protrusion whose height is set based on a thickness dimension of the pressure cuff at the time of contraction;
    the at least one antenna substrate is disposed on the protrusion of the band member.

7. The biological information measuring device according to claim 1, wherein
    the band member has, on the surface that faces the measured part, a band-shaped recess having a shape corresponding to the pressure cuff, and a protrusion having a predetermined height for the at least one antenna substrate to abut against the measured part;
    the pressure cuff is disposed in the recess of the band member;
    the at least one antenna substrate is disposed on the protrusion of the band member.

8. The biological information measuring device according to claim 1, further comprising:
    a control circuit support member, disposed between the band member and the pressure cuff and electrically connected to the at least one antenna substrate, wherein
    the control circuit support member at least has:
        a transmitting circuit, generating the measurement signal, supplying the measurement signal to the antenna and causing the antenna to transmit it as the radio wave; and
        a receiving circuit, receiving and detecting the reflection signal composed of the radio wave received by the antenna.

9. The biological information measuring device according to claim 2, wherein a plurality of the at least one antenna substrate are disposed at predetermined intervals in a direction orthogonal to the artery comprised in the measured part.

10. The biological information measuring device according to claim 3, wherein a plurality of the antenna are disposed on one antenna substrate at predetermined intervals in a direction orthogonal to the artery comprised in the measured part.

* * * * *